(12) United States Patent
Nyhus

(10) Patent No.: US 6,353,158 B1
(45) Date of Patent: Mar. 5, 2002

(54) INBRED CORN LINE ZS02234

(75) Inventor: Kris Nyhus, New Haven, IN (US)

(73) Assignee: Garst Seed Company, Slater, IA (US)

( * ) Notice: Subject to any disclaimer, the term of this patent is extended or adjusted under 35 U.S.C. 154(b) by 0 days.

(21) Appl. No.: 08/993,136

(22) Filed: Dec. 10, 1997

(51) Int. Cl.[7] .............................. A01H 5/00; A01H 4/00; A01H 1/00; C12N 5/04

(52) U.S. Cl. .................... 800/320.1; 800/298; 800/275; 800/271; 800/301; 800/302; 800/303; 435/412; 435/424; 435/430; 435/430.1

(58) Field of Search .............................. 800/220.1, 298, 800/275, 271, 274, 303, 301, 302; 435/412, 424, 430, 430.1

(56) References Cited

PUBLICATIONS

Coe, E. H., Jr. and M. G. Neuffer, The Genetics of Corn, p. 111.

Conger, B. V., F. J. Novak, R. Afza and K. Erdelsky, "Somatic embryogenesis from cultured leaf segments of *Zea mays*", Plant Cell Reports, 6:345–347, (1987).

Duncan, D. R., M. E. Williams, B. E. Zehr and J. M. Widholm, "The Production of callus capable of plant regeneration from immature embryos of numerous *Zea mays* genotypes", Planta, 165: 322–332, (1985).

Edallo, et al, "Chromosomal Variation and Frequency of Spontaneous Mutation Associated with in Vitro Culture and Plant Regeneration in Maize", Maydica XXVI, pp. 39–56, (1981).

Forsberg, R. A. and R. R. Smith, "Sources, Maintenance, and Utilization of Parental Material", Hybridization of Crop Plants, Chapter 4, pp. 65–81, (1980).

Green, C. E. and R. L. Phillips, "Plant Regeneration from Tissue Cultures of Maize", Crop Science, vol. 15, pp. 417–421, (1975).

Green, C. E. and C. A. Rhodes, "Plant Regeneration in Tissue Cultures of Maize", Maize for Biological Research, pp. 367–372, (1982).

Hallauer, et al., "Corn Breeding", Corn and Corn Improvement, pp.463–564 (1988). Sprague et al, eds. Lowe, Keith, Patent Application, 0 160 390.

Meghji, M. R., J. W. Dudley, R. J. Lampert and G. F. Sprague, "Inbreeding Depression, Inbred and Hybrid Grain Yields, and Other Traits of Maize Genotypes Representing Three Eras", Crop Science, vol. 24, pp. 545–549 (1984).

Phillips, et al., "Cell/Tissue Culture and In Vitro Manipulation", In Corn & Corn Improvement, 3rd Ed., ASA Publication, #18, pp. 345–349 & 356–357, (1988).

Poehlman, John Milton, "Breeding Field Crop", AVI Publishing Company, Inc., Westport, Connecticut, pp. 237–246, (1987).

Rao, K. V., et al., "Somatic Embryogenesis in Glume Callus Cultures", Osmania University, Hyberabad, India.

Sass, "Morphology", In Corn & Corn Improvement, ASA Publication, Madison, Wisconsin, pp. 89–109, (1977).

Songstad, David D., David R. Duncan, and Jack M. Widholm, "Effect of 1–aminocyclopropane–1–caroxylic acid, silver nitrate, and norbornadiene on plant regeneration from maize callus cultures", Plant Cell Reports, 7:262–265, (1988).

Tomes, et al., "The Effect of Parental Genotype on Initiation of Embryogenic Callus from Elite Maize (*Zea mays*1.) Germplasm", Theor. Appl. Genet. 70., pp. 505–509, (1985).

Troyer, et al., "Selection for Early Flowering in Corn: 10 Late Synthesis", Crop Science, vol. 25, pp. 695–697.

Umbeck, et al., "Reversion of Male–Sterile T–Cytoplasm Maize to Male Fertility in Tissue Culture", Crop Science, vol. 23, pp. 584–588, (1983).

Wright, H., "Commercial Hybrid Seed Production", Hybridization of Crop Plants, pp. 161–176, (1980).

Wych, R. D., "Production of Hybrid Seed Corn", Corn and Corn Improvement, pp. 565–607, (1988).

*Primary Examiner*—Gary Benzion
(74) *Attorney, Agent, or Firm*—Kent A. Herink, Esq.; Daniel A. Rosenberg, Esq.

(57) ABSTRACT

Broadly this invention provides inbred corn line ZS02234. The methods for producing a corn plant by crossing the inbred line ZS02234 are encompassed by the invention. Additionally, the invention relates to the various parts of inbred ZS02234 including culturable cells. This invention relates to hybrid corn seeds and plants produced by crossing the inbred line ZS02234 with at least one other corn line.

16 Claims, No Drawings

INBRED CORN LINE ZS02234

FIELD OF THE INVENTION

This invention is in the field of corn breeding, specifically relating to an inbred corn line designated ZS02234.

BACKGROUND OF THE INVENTION

The original maize plant was indigenous to the Western Hemisphere. The plants were weedlike and only through the efforts of early breeders was a cultivated crop species developed. The physical traits of maize are such that self pollination or cross pollination can occur. Each plant has a separate male and female flower, the tassel and ear, respectively. Natural pollination occurs when wind transfers pollen from tassel to the silks on the corn ears. This type of pollination contributed to the wide variation of maize varieties present in the Western Hemisphere.

The development of a planned breeding program for maize only occurred in the last century. Originally, maize was an open pollinated variety having heterogeneous genotypes. The maize farmer selected uniform ears from the yield of these genotypes and reserved them for planting the next season. The result was a field of maize plants that were segregating for a variety of traits. This type of maize selection lead to at most incremental increases in seed yield.

Large increases in seed yield were the result of the development of hybrid corn varieties in planned breeding programs. Hybrids were developed by selecting corn lines and selfing these lines for several generations to develop homozygous pure inbred lines and crossing selected inbred lines with unrelated inbred lines to produce hybrid progeny (F1). Inbred lines can be difficult to produce since the inbreeding process in corn decreases the vigor. However, when two inbred lines are crossed, the hybrid plant evidences greatly increased vigor compared to open pollinated segregating maize plants. An important factor of the homozygosity and the homogeneity of the inbred lines is that the hybrid from any cross will always be the same, and can be reproduced.

The ultimate objective of the commercial maize seed companies is to produce high yielding, agronomically sound plants which perform well in certain regions or areas of the Corn Belt. To produce these types of hybrids, the companies must develop inbreds which carry needed traits into the hybrid combination. Hybrids are not uniformly adapted for the Corn Belt, but are specifically adapted for regions of the Corn Belt. Northern regions of the Corn Belt require shorter season hybrids than do southern regions of the Corn Belt. Hybrids that grow well in Colorado and Nebraska soils may not flourish in rich Illinois soil. Thus, a variety of major agronomic traits are important in hybrid combination for the various Corn Belt regions, and have an impact on hybrid performance.

Inbred line development and hybrid testing have been emphasized in the past half century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcross populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include yield potential in hybrid combination; dry down; maturity; grain moisture at harvest; greensnap; resistance to root lodging; resistance to stalk lodging; grain quality; disease and insect resistance; ear and plant height; performance in different soil types such as: low level of organic matter, clay, sand, black, high pH, low pH; performance in: wet environments, drought environments, and no tillage conditions. These traits appear to be governed by a complex genetic system that makes selection and breeding of an inbred line extremely difficult. Even if an inbred, in hybrid combination, has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. Thus, the general procedure of producing a non segregating $F_1$ generation and self pollinating to produce a $F_2$ generation that segregates for traits does not easily lead to a useful inbred. Great care and breeder expertise must be used in selection of breeding material to continue to increase yield and agronomics of inbreds and resultant commercial hybrids.

SUMMARY OF THE INVENTION

The present invention relates to an inbred corn line ZS02234. Specifically, this invention relates to plants and seeds of this line. Additionally, this relates to a method of producing hybrid seed corn from this inbred. More particularly, this invention relates to the unique combination of traits in corn line ZS02234.

Generally then, the present invention includes an inbred corn seed designated ZS02234. This seed produces a corn plant.

The invention also includes the tissue culture of regenerable cells of ZS02234 wherein the tissue regenerates plants having the genotype of ZS02234. The tissue culture is selected from the group consisting of leaves, pollen, embryos, roots, root tips, anthers, silk, flowers, kernels, ears, cobs, husks and stalks, and cells and protoplasts thereof. The corn plant regenerated from ZS02234 having ZS02234's genotype.

The invention extends to hybrid seed produced by planting, in pollinating proximity, seeds of corn inbred lines ZS02234 and another inbred line; cultivating corn plants resulting from said planting; preventing pollen production by the plants of one of the inbred lines; allowing natural cross pollinating to occur between said inbred lines; and harvesting seeds produced on plants of the inbred. The hybrid seed produced by hybrid combination of plants of inbred corn seed designated ZS02234 and plants of another inbred line. Hybrid plants grown from this hybrid seed.

The invention further includes a method of hybrid F1 production. A first generation (F1) hybrid corn plant produced by the process of planting, in pollinating proximity, seeds of corn inbred lines ZS02234 and another inbred line; cultivating corn plants resulting from said planting; preventing pollen production by the plants of one of the inbred lines; allowing natural cross pollinating to occur between said inbred lines; harvesting seeds produced on plants of the inbred; and growing a harvested seed.

A tissue culture of the regenerable cells of hybrid plants produced with use of ZS02234 genetic material. A tissue culture of the regenerable cells of the corn plant produced by the method described above.

DEFINITIONS

In the description and examples which follow, a number of terms are used. In order to provide a clear and consistent understanding of the specifications and claims, including the scope to be given such terms, the following definitions are provided.

BL MOIST

The moisture percentage of the grain at black layer, i.e., when 50% of the plants per plot have reached physiological maturity.

COLD GERM

Cold Germ is a measurement of seed germination under cold soil conditions. Data is reported as percent of seed germinating.

ECB

European corn borer a maize eating insect. ECBI is the first brood generation of European corn borers. ECBII is the second generation of European corn borers.

EMERGE

The number of emerged plants per plot (planted at the same seedling rate) collected when plants have two fully developed leaves.

GI

This is a selection index which provides a single quantitative measure of the worth of a hybrid based on four traits. Yield is the primary trait contributing to index values. The GI value is calculated by combining stalk lodging, root lodging, yield and dropped ears according to the attached mathematical formula:

GI=100+0.5(YLD)-0.9(%STALK LODGE)-0.9(%ROOT LODGE)-2.7(%DROPPED EAR)

GLS

Gray Leaf Spot (*Cercospora Zeae*) disease rating. This is rated on a 1–9 scale with a "1" being very susceptible, and a "9" being very resistant.*

GW

Goss' Wilt (*Corynebacterium nebraskense*). This is rated on a 1–9 scale with a "1" being very susceptible, and a "9" being very resistant.*

HEATP10

The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp (°F.)} + \text{Min Temp (°F.)})}{2} - 50$$

The highest maximum temperature used is 86° F. and the lowest minimum temperature used is 50° F. For each inbred or hybrid it takes a certain number of GDU's to reach various stages of plant development.

HEATBL

The number of GDU's after planting when approximately 50 percent of the inbred or hybrid plants in a plot have grain which has reached physiological maturity (black layer).

HEATPEEK

The number of GDU's after planting of an inbred when approximately 50 percent of the plants show visible tassel extension.

HEATP50 or HTP50

The number of GDU's required for an inbred or hybrid to have approximately 50 percent of the plants shedding pollen. Growing Degree Units are calculated by the Barger Method as shown in the HEATP10 definition.

HEATP90

The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10

The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50

The number of GDU's required for an inbred or hybrid to have approximately 50 percent of the plants with silk emergence of at least 0.5 inches. Growing Degree Units are calculated by the Barger Method as shown in the HEATP10 definition.

HEATS90

The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$

Maize Dwarf Mosaic Virus strain A. The corn is rated on a 1–9 scale with a "1" being very susceptible, and a "9" being very resistant.*

$MDMV_B$

Maize Dwarf Mosaic Virus strain B. This is rated on a 1–9 scale with a "1" being very susceptible and a "9" being very resistant.*

MOISTURE

The average percentage grain moisture of an inbred or hybrid at harvest time.

NLB

Northern Leaf Blight (*Exserohilum turcicum*) disease rating. This is rated on a 1–9 scale with a "1" being very susceptible, and a "9" being very resistant.*

PCT TILLER

The total number of tillers per plot divided by the total number of plants per plot.

PLANT

This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

PLANT HEIGHT

The distance in centimeters from ground level to the base of the tassel peduncle.

RM

Predicted relative maturity based on the moisture percentage of the grain at harvest. This rating is based on known set of checks and utilizes standard linear regression analyses and is referred to as the Minnesota Relative Maturity Rating System.

SHED

The volume of pollen shed by the male flower rated on a 1–9 scale where a "1" is a very light pollen shedder, a "4.5" is a moderate shedder, and a "9" is a very heavy shedder.

SLB

Southern Leaf Blight (*Bipolaris maydis*) disease rating. This is rated on a 1–9 scale with a "1" being very susceptible, and a "9" being very resistant.*

TWT

The measure of the weight of grain in pounds for a one bushel volume adjusted for percent grain moisture.

VIGOR

Visual rating of 1 to 9 made 2–3 weeks post-emergence where a "1" indicates very poor early plant development, and a "9" indicates superior plant development.

WARM GERM

A measurement of seed germination under ideal (warm, moist) conditions. Data is reported as percent of seeds germinating.

YIELD (YLD)

Actual yield of grain at harvest adjusted to 15.5% moisture. Measurements are reported in bushels per acre.

% DROPPED EARS (DE)

The number of plants per plot which dropped their primary ear divided by the total number of plants per plot.

% LRG FLAT

Percentage by weight of shelled corn that passes through a $26/64$ inch round screen and a $14/64$ inch slot screen, but does not pass through a screen with $20.5/64$ inch round openings.

% LRG ROUND

Percentage by weight of shelled corn that passes through a $26/64$ inch round screen, but does not pass through a $14/64$ inch slot screen or a screen with $20.5/64$ inch round openings.

% MED FLAT

Percentage by weight of shelled corn that passes through a $20.5/64$ inch round screen and a $13/64$ inch slotted screen, but does not pass through a screen with $17/64$ inch round openings.

% MED ROUND

Percentage by weight of shelled corn that passes through a $20.5/64$ inch round screen, but does not pass through a $13/64$ inch slot screen or a screen with $17/64$ inch round openings.

% SML FLAT

Percentage by weight of shelled corn that passes through a $17/64$ inch round screen and a $12/64$ inch slotted screen, but does not pass through a screen with $15/64$ inch round openings.

% SML ROUND

Percentage by weight of shelled corn that passes through a $17/64$ inch round screen, but does not pass through a $12/64$ inch slotted screen or a screen with $15/64$ inch round openings.

% ROOT LODGE (RL)

Percentage of plants per plot leaning more that 30 degrees from vertical divided by total plants per plot.

% STALK LODGE (SL)

Percentage of plants per plot with the stalk broken below the primary ear node divided by the total plants per plot.

Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

ZS02234 can be used as a female, having acceptable seed production characteristics and a large proportion of medium flat seed size. When placed in hybrid combination with males, this inbred forms excellent hybrids. In hybrid combinations this inbred can be used as a male. But due to this inbred's average pollen shed characteristics it is infrequently used as a male. This inbred in hybrid combination, is a robust hybrid exhibiting low moisture characteristics.

The inbred has shown uniformity and stability within the limits of environmental influence for all the traits as described in the Variety Description Information (Table 1) that follows. Most of the data in the Variety Description information was collected at Slater, Iowa or other Garst research stations.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in ZS02234.

The best method of producing the invention, ZS02234 which is substantially homozygous, is by planting the seed of ZS02234 and self-pollinating or sib pollinating the resultant plant in an isolated environment, and harvesting the resultant seed or the resultant pollen. The hybrid containing ZS02234 is best produced by planting the inbred ZS02234 and an appropriate crossing line in an isolated environment, detasseling one inbred and cross-pollinating with the pollen of the other inbred and harvesting the resultant seed or the resultant pollen. Alternatively, the pollen of ZS02234 can be stored and then applied to an inbred to form hybrid seed. This seed can be planted to form the hybrid plant which then forms grain that is segegrating.

TABLE 1

ZS02234
VARIETY DESCRIPTION INFORMATION

- Type: Dent, northern corn belt
- GRM: ZS02234 has a GRM 100. Hybrids range from 90–105.
- Entomology: ECB1-8.00-Ratings  scale 9 = highly resistant
  ECB2-7.49-      1 = highly susceptible
- Maturity:

| Days | Heat Limits | |
  |---|---|---|
  | ~70–78 | 1398–1508 | From planting to 50% of plants in silk |
  | ~70–79 | 1491–1476 | From planting to 50% of plants in pollen |
  | ~3 | | From 10% to 90% pollen shed |

- DISEASE RESISTANCE  Northern leaf blight = 3.5
  Gray leafspot = 3.5
  GW = 6.0
  MDMVB = 1.0
- An Inbred comparable to ZS02234 is ZS0560.

INBRED ZS02234

#3 MATURITY

| DAYS | HEATUNITS | |
|---|---|---|
| 78 | 1398 | FROM PLANTING TO 50% OF PLANTS IN SILK |
| 79 | 1424 | FROM PLANTING TO 50% OF PLANTS IN POLLEN |
| 3 | | FROM 10% TO 90% POLLEN SHED |

#4 PLANT

DATA

| | |
|---|---|
| 3 | ANTHOCYANIN OF BRACE ROOTS: 1 = ABSENT 2 = FAINT 3 = MODERATE 4 = DARK |

#5 LEAF

COLOR/DATA

| | |
|---|---|
| 3/DARK GREEN | LEAF COLOR **MUNSELL CODE-5GY 4/6 |
| 6 | LEAF SHEATH PUBESCENCE (1 = NONE TO 9 = PEACH FUZZ) |
| 6 | MARGINAL WAVES (1 = NONE TO 9 = MANY) |
| 3 | LONGITUDINAL CREASES (1 = NONE TO 9 = MANY) |

#6 TASSEL

COLOR/DATA

| | |
|---|---|
| 4 | POLLEN SHED (0 = STERILE TO 9 = HEAVY SHEDDER) |
| 8/YELLOW-ORNGE | ANTHER COLOR **MUNSELL CODE-7.5YR 7/6 |
| 1&8/LGRN/YLOR | GLUME COLOR **MUNSELL CODE-2.5GY 7/6 W/S 5YR 6/10 |
| 2 | BAR GLUME: 1 = ABSENT 2 = PRESENT |

#7A EAR (UNHUSKED DATA)

COLOR/DATA

| | |
|---|---|
| 5/GREEN-YELLOW SILK COLOR | (3 DAYS AFTER EMERGE) **MUNSELL CODE-2.5GY 8/6 |
| 2/MEDIUM GREEN FRESH HUSK | (25 DAYS AFTER 50% SILK) **MUNSELL CODE-5GY 6/6 |
| 6/PALE YELLOW DRY HUSK COLOR | (65 DAYS AFTER 50% SILK **MUNSELL CODE-SY 8/7 |
| 1 | POSITION OF EAR AT DRY HUSK: 1 = UPRIGHT 2 = HORIZONTAL 3 = PENDENT |
| 5 | HUSK TIGHTNESS (1 = VERY LOOSE TO 9 = VERY TIGHT) |
| 2 | HUSK EXTENSION AT HARVEST: 1 = EXPOSED EAR 2 = 8 CM 3 = 8–10 CM 4 = >10 CM |

#7B EAR (HUSKED DATA)

DATA

| | |
|---|---|
| 2 | KERNEL. ROWS: 1 = INDISTINCT 2 = DISTINCT |
| 1 | ROW ALIGNMENT: 1 = STRAIT 2 = SLIGHT CURVE 3 = SPIRAL |
| 2 | EAR TAPPER: 1 = SLIGHT 2 = AVERAGE 3 = EXTREME |

#8 KERNEL (DRY)

COLOR/DATA

| | |
|---|---|
| 1 | ALEURONE COLOR PATTERN: 1 = HOMO 2 = SEG |
| 8/YELLOW-ORNGE | ALEURONE COLOR **MUNSELL CODE-7.5YR 6/10 |
| 8/YELLOW-ORNGE | HARD ENDOSPERM COLOR **MUNSELL CODE-7.5YR 5/8 |
| 3 | ENDOSPERM TYPE |
| 7/YELLOW | CROWN COLOR **MUNSELL CODE-2.5Y 8/10 |

#9 COB

COLOR

| | | |
|---|---|---|
| 24/BRONZE | COB COLOR **MUNSELL CODE-2.5YR 4/6 | |

TABLE 1-continued

1997 PVP TRAITS
INBRED ZS02234

| | N | MEAN | STD. | T-STAT | PROB | 95% CI |
|---|---|---|---|---|---|---|
| EAR HEIGHT (CM) | 15 | 67.00 | 10.89 | 23.83 | 0.0000 | (61.49, 72.51) |
| LENGTH OF PRIMARY EAR LEAF (CM) | 15 | 88.60 | 4.03 | 85.11 | 0.0000 | (86.56, 90.64) |
| WIDTH OF PRIMARY EAR LEAF (CM) | 15 | 7.63 | 0.49 | 60.75 | 0.0000 | (7.38, 7.87) |
| TOP EAR INTERNODE (CM) | 15 | 14.21 | 3.69 | 14.93 | 0.0000 | (12.35, 16.08) |
| DEGREE OF LEAF ANGLE | 15 | 22.20 | 7.17 | 11.99 | 0.0000 | (18.57, 25.83) |
| # OF EARS PER PLANT | 15 | 1.73 | 0.59 | 11.31 | 0.0000 | (1.43, 2.03) |
| # OF LEAVES ABOVE TOP EAR | 15 | 5.80 | 0.56 | 40.07 | 0.0000 | (5.52, 6.08) |
| # OF PRIMARY LATERAL TASSEL BRANCHES | 15 | 7.13 | 1.13 | 24.55 | 0.0000 | (6.56, 7.70) |
| PLANT HEIGHT (CM) | 15 | 185.8 | 16.85 | 42.71 | 0.0000 | (177.3, 194.3) |
| TASSEL LENGTH (CM) | 15 | 40.67 | 4.24 | 37.17 | 0.0000 | (38.52, 42.8i) |
| TASSEL BRANCH ANGLE | 15 | 58.53 | 29.59 | 7.66 | 0.0000 | (43.56, 73.5i) |
| # OF TILLER PER PLANTS | 15 | 0.00 | 0.00 | | | (0.00, 0.00) |
| WEIGHT PER 100 KERNELS (GM) | 15 | 24.00 | 2.78 | 33.45 | 0.0000 | (22.59, 25.41) |
| EAR LENGTH (CM) | 15 | 14.20 | 2.76 | 19.91 | 0.0000 | (12.80, 15.60) |
| EAR WEIGHT (GM) | 15 | 92.57 | 24.30 | 14.75 | 0.0000 | (80.27, 104.9) |
| # OF KERNEL ROWS | 15 | 13.87 | 1.19 | 45.24 | 0.0000 | (13.27, 14.47) |
| COB DIAMETER AT MID-POINT (MM) | 15 | 22.79 | 1.09 | 81.19 | 0.0000 | (22.24, 23.34) |
| EAR DIAMETER AT MID-POINT (MM) | 15 | 37.54 | 2.03 | 71.58 | 0.0000 | (36.51, 38.57) |
| KERNEL LENGTH (MM) | 15 | 9.87 | 0.83 | 46.21 | 0.0000 | (9.45, 10.29) |
| KERNEL THICKNESS (MM) | 15 | 5.05 | 1.04 | 18.85 | 0.0000 | (4.53, 5.58) |
| KERNEL WIDTH (MM) | 15 | 7.40 | 0.50 | 57.65 | 0.0000 | (7.15, 7.65) |
| % ROUND KERNELS (SHAPE GRADE) | 15 | 39.21 | 13.68 | 11.10 | 0.0000 | (32.28, 46.13) |
| SHANK LENGTH | 15 | 14.91 | 2.57 | 22.50 | 0.0000 | (13.61, 16.21) |

The purity and homozygosity of inbred ZS02234 is constantly being tracked using isozyme genotypes as shown in Table 2.

Isozyme Genotypes for ZS02234

Isozyme data were generated for inbred corn line ZS02234 according to procedures known and published in the art. The data in Table 2 gives the electrophoresis data on ZS02234.

TABLE 2

ELECTROPHORESIS RESULTS FOR ZS02234

| INBRED | ACP1 | ACP4 | ADH | MDH1 | MDH2 | PGD1 | PGD2 | PH1 | PGM | IDH |
|---|---|---|---|---|---|---|---|---|---|---|
| ZS02234 | 11 | 00 | 22 | 22 | 11 | 11 | 11 | 22 | 22 | 11 |

Inbred and Hybrid Performance of ZS02234

The traits and characteristics of inbred corn line ZS02234 are listed to compare with other inbreds and/or in hybrid combination ZS02234 data shows the characteristics and traits of importance, giving a snapshot of ZS02234.

Table 3A compares inbred ZS02234 with inbred ZS0560. ZS02234 has greater plant height and ear height than ZS0560. ZS02234 silks significantly earlier than ZS0560, showing significantly less GDUs at all HEATS ratings. And, ZS02234 reaches HEAT PEEK with signficantly more GDU's then ZS0560. ZS02234 shows significantly higher grain moisture at harvest but significantly less inbred yields than ZS0560. ZS02234 tends to produce more medium flats than medium rounds.

TABLE 3A

PAIRED INBRED COMPARISON DATA

| YEAR | INBRED | VIGOR | PCT EMERGE | PCT TILLER | PLANT HEIGHT | EAR HEIGHT | SHED | EAR QUALITY | PCT BARREN |
|---|---|---|---|---|---|---|---|---|---|
| OVERALL | ZS02234 | 6.0 | 75.9 | | 179.9 | 78.6 | 6.1 | | |
| | ZS0560 | 6.2 | 87.5 | | 164.3 | 68.6 | 5.5 | | |

TABLE 3A-continued

| | | PAIRED INBRED COMPARISON DATA | | | | |
|---|---|---|---|---|---|---|
| | # EXPTS | 13 | 13 | 13 | 13 | 10 |
| | DIFF | 0.2 | 11.6 | 15.5 | 10.0 | 0.6 |
| | PROB | 0.570 | 0.007*** | 0.001*** | 0.007*** | 0.239 |

| YEAR | INBRED | HEATP10 | HEATP50 | HEATP90 | HEATS10 | HEATS50 | HEATS90 |
|---|---|---|---|---|---|---|---|
| OVERALL | ZS02234 | 1440 | 1491 | 1628 | 1452 | 1482 | 1544 |
| | ZS0560 | 1472 | 1522 | 1678 | 1473 | 1508 | 1561 |
| | # EXPTS | 10 | 10 | 10 | 10 | 10 | 10 |
| | DIFF | 32 | 31 | 50 | 22 | 25 | 17 |
| | PROB | 0.003*** | 0.001*** | 0.000*** | 0.001*** | 0.001*** | 0.094* |

| YEAR | INBRED | HEATPEEK | HEATBL | BL MOIST | % ROOT LODGE | % STALK LODGE | % DROPPED EARS | MOISTURE | YIELD |
|---|---|---|---|---|---|---|---|---|---|
| OVERALL | ZS02234 | 1366 | 2579 | | | | | 10.6 | 56.9 |
| | ZS0560 | 1403 | 2584 | | | | | 12.6 | 78.4 |
| | # EXPTS | 10 | 2 | | | | | 13 | 13 |
| | DIFF | 37 | 5 | | | | | 2.1 | 21.5 |
| | PROB | 0.002*** | 0.500 | | | | | 0.000*** | 0.000*** |

| YEAR | INBRED | WARM GERM | COLD GERM | % LRG ROUND | % LRG FLAT | % MED ROUND | % MED FLAT | % SML ROUND | % SML FLAT |
|---|---|---|---|---|---|---|---|---|---|
| OVERALL | ZS02234 | 92.8 | 80.1 | | | 25.0 | 41.9 | | |
| | ZS0560 | 95.5 | 84.5 | | | 43.6 | 20.0 | | |
| | # EXPTS | 11 | 11 | | | 13 | 13 | | |
| | DIFF | 2.8 | 4.4 | | | 18.5 | 21.8 | | |
| | PROB | 0.009*** | 0.229 | | | 0.000*** | 0.000*** | | |

*.05 < prob <= .10
**.01 < PROB <= .05
***.00 < PROB <= .01

Table 4 shows the GCA (general combining ability) estimates of ZS02234 compared with the GCA estimates of other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and Garst's commercial products and pre-commercial hybrids which were grown in the same sets and locations.

Table 4 shows ZS02234 crossed in hybrid combinations. ZS02234 shows yield, moisture, and yield by moisture (YM) advantage over ZS0560.

TABLE 4

| | N | FI | YM | GI | I | YLD | MST |
|---|---|---|---|---|---|---|---|
| ZS02234 XR = | 284 | 4.3 | 0.8 | 0.5 | 2.2 | 3.1 | 1.7 |
| ZS0560 XR = | 14648 | 0.5 | 0.0 | 0.4 | 0.4 | 0.6 | 0.0 |

| | % SL | % RL | % DE | TWT | POP | RM |
|---|---|---|---|---|---|---|
| ZS02234 XR = | 0.1 | -1.0 | -0.1 | 0.0 | -22 | 100 |
| ZS0560 XR = | 0.2 | 0.0 | 0.0 | 0.2 | -26 | 110 |

Table 5 shows ZS02234, in a hybrid combination, in comparison with the plants in the environment around it at the same location. ZS02234 in hybrid combination yields well in low to medium yielding environments. In these yielding environments ZS02234, in hybrid combination, out yields ZS0560 as a hybrid. In high yielding environments, ZS02234 hybrid tends to show less aggressive yields compared to the environment and compared to hybrid combination of ZS0560/X.

TABLE 5

| YIELD RESPONSE | | | | | | |
|---|---|---|---|---|---|---|
| 1. | | | | | | |
| HYBRID | | | YIELD | | | |
| Environment | 75 | 100 | 125 | 150 | 175 | 200 |
| ZS02234/X | 90 | 110 | 130 | 150 | 170 | 190 |
| 2. | | | | | | |
| HYBRID | | | YIELD | | | |
| Environment | 75 | 100 | 125 | 150 | 175 | 200 |
| ZS0560/X | 70 | 94 | 119 | 144 | 168 | 193 |

Table 6A shows the advantage ZS02234 hybrid has compared to one commercially available Garst hybrid. The ZS02234 hybrid is better in yield, is significantly better in yield/moisture and shows a positive test weight advantage compared to hybrid 8735. These two hybrids carry a common inbred.

TABLE 6A

PAIRED HYBRID COMPARISON DATA

| YEAR | HYBRID | % ROOT LODGE | % STALK LODGE | % DROPPED EARS | TEST WEIGHT | MOISTURE | YIELD | |
|---|---|---|---|---|---|---|---|---|
| OVERALL | ZS02234/X | 0.5 | 1.8 | 0.0 | 49.0 | 20.7 | 142.4 | 169.1 |
| | 8735 | 0.6 | 1.6 | 0.0 | 48.6 | 24.8 | 135.9 | 165.9 |
| | # EXPTS | 25 | 25 | 25 | 20 | 25 | 25 | 25 |
| | DIFF | 0.2 | 0.2 | 0.0 | 0.3 | 4.1 | 6.5 | 3.1 |
| | PROB | 0.600 | 0.653 | 0.357 | 0.634 | 0.000*** | 0.147 | 0.190 |

| YEAR | INBRED | MATURITY | Y M | FI |
|---|---|---|---|---|
| OVERALL | ZS02234/X | — | 7.5 | 121 |
| | 8735 | — | 5.8 | 109 |
| | # EXPTS | — | 25 | 25 |
| | DIFF | — | 1.7 | 12.6 |
| | PROB | — | 0.000*** | 0.000*** |

*.05 < PROB <= .10
**.01 < PROB <= .05
***.00 < PROB <= .01

Table 6B shows the advantages and disadvantages generated by comparison of the agronomic data of the two hybrids. ZS02234 brings its vigor into the hybrid package.

TABLE 6B

ZS02234/x vs. 8735
AGRONOMIC DATA

Advantage of ZS02234/x over 8735

| HYBRID | N | ESTAND | EMG | VIGOR | PLANT HEIGHT | EAR HEIGHT | STAYGREEN |
|---|---|---|---|---|---|---|---|
| | 1o | 7.5 | 1.3 | 1.0 | 1.6 | 3.2 | 2.1 |

The inbred ZS02234 can be employed as the female in a hybrid production field. This inbred is a vigorous line with good inbred seed yield. ZS02234, in hybrid combination, produces hybrids that have a low percentage of stalk lodging and above average testweights. The ZS02234 hybrid carries excellent yields in low environments. ZS02234 inbred has good general combining ability.

The present invention can by mutagenisis be transformed into an isogenic line with the brown mid rib mutation, low phytic acid mutation, the imazethapyr (IT) mutation, and the various starch mutations such as ae, waxy, dull, and the like. The use of EMS as a mutating agent chemical permits single point mutations in corn has been known and used since at least the early seventies. Other mutating chemicals are also capable of causing these type of mutations and generating a line that is isogenic or nearly isogenic to the present invention.

The present invention can also be transformed to carry well known transgenic genes (as well as less well known genes) such as the bacillus thuringiensis genes that encode for an insect resistant crystalline protein for example Cry genes like Cry V, Cry lab, Cry lac, Cry 9c. The present invention can also be transformed to carry herbicide genes such as ESPS, bar, pat, and the like. The regeneration of transformed cells is now a precise science which generates plants that are characterized by the original plant characteristics with the added benefit of the transgenes trait. The use of pollen transformation as a transformation method eliminates the need for regeneration of the cells and appears to produce lines which are nearly isogenic to the present invention while additionally carrying the characteristic expressed by the added transgene.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line ZS02234. Further, both first and second parent corn plants can come from the inbred corn line ZS02234. A variety of breeding methods can be selected depending on the mode of reproduction, the trait, the condition of the germplasm. Thus, any such methods using the inbred corn line ZS02234 are part of this invention: selfing, backcrosses, hybrid production, crosses to populations, haploid and anther culturing and the like.

Various culturing techniques known to those skilled in the art, such as haploid, transformation, and a host of other conventional and unconventional methods are within the scope of the invention. All plants and plant cells produced using inbred corn line ZS02234 are within the scope of this invention. The invention encompasses the inbred corn line used in crosses with other, different, corn inbreds to produce (F1) corn hybrid seeds and plants. This invention includes cells which upon growth and differentiation produce corn plants having the physiological and morphological characteristics of the inbred line ZS02234.

Duncan, from at least 1985–1988 produced literature on plant regeneration from callus. Both inbred and hybrid callus have resulted in regenerated plants at excellent efficiency rates. Somatic embryogenesis has been performed on various maize tissue such as glume which before the 1980's was considered unusable for this purpose. The prior art clearly teaches the regeneration of plants from various maize tissues.

European Patent Application, publication 160,390, describes tissue culture of corn which can be used by those skilled in the art. Corn tissue culture procedures are also described in the literature as early as 1982. Various culturing techniques known to those skilled in the art, such as haploid, (stock six is a method that has been in use for twenty years and is well known to those with skill in the art), transformation, and a host of other conventional and unconventional methods are within the scope of the invention. All plants and plant cells produced using the inbred corn line are within the scope of this invention. The term transgenic plant refers to plants having exogenous genetic sequences which are introduced into the genome of a plant by a transformation method and the progeny thereof.

Transformation Methods—are means for integrating new genetic coding sequences into the plant's genome by the incorporation of these sequences into a plant through man's assistance.

Though there are a large number of known methods to transform plants, certain types of plants are more amenable to transformation than are others. Tobacco is a readily transformable plant. The basic steps of transforming plants including monocots are known in the art. These steps are concisely outlined in U.S. Pat. No. 5,484,956 "Fertile Transgenic *Zea mays* Plants Comprising Heterologous DNA Encoding *Bacillus Thuringiensis* Endotoxin" issued Jan. 16, 1996 and U.S. Pat. No. 5,489,520 "Process of Producing Fertile *Zea mays* Plants and Progeny Comprising a Gene Encoding Phosphinothricin Acetyl Transferase" issued Feb. 6, 1996.

Plant cells such as maize can be transformed by a number of different techniques. Some of these techniques which have been reported on and are known in the art include maize pollen transformation (See University of Toledo 1993 U.S. Pat. No. 5,177,010); Biolistic gun technology (See U.S. Pat. No. 5,484,956); Whiskers technology (See U.S. Pat. No. 5,464,765 and 5,302,523); Electroporation; PEG on Maize; Agrobacterium (See 1996 article on transformation of maize cells in *Nature Biotechnology*, Volume Jun. 14, 1996) along with numerous other methods which may have slightly lower efficiency rates then those listed. Some of these methods require specific types of cells and other methods can be practiced on any number of cell types.

The use of pollen, cotyledons, meristems and ovum as the target issue can eliminate the need for extensive tissue culture work. However, the present state of the technology does not provide very efficient use of this material.

Generally, cells derived from meristematic tissue are useful. Zygotic embryos can also be used. Additionally, the method of transformation of meristematic cells of cereal is also taught in the PCT application WO96/04392. Any of the various cell lines, tissues, plants and plant parts can and have been transformed by those having knowledge in the art. Methods of preparing callus from various plants are well known in the art and specific methods are detailed in patents and references used by those skilled in the art. Cultures can be initiated from most of the above identified tissue. The only true requirement of the transforming material is that it can form a transformed plant. The transgenic gene can come from various non-plant genes (such as; bacteria, yeast, animals, viruses) along with being from animal or plants.

The DNA used for transformation of these plants clearly may be circular, linear, double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The regulatory promoters employed can be constitutive such as CaMv35S (usually for dicots) and polyubiquitin for monocots or tissue specific promoters such as CAB promoters, etc. The prior art includes but is not limited to octopine synthase, nopaline synthase, CaMvl9S, mannopine synthase promoters. These regulatory sequences can be combined with introns, terminators, enhancers, leader sequences and the like in the material used for transformation.

The isolated DNA is then transformed into the plant. Many dicots can easily be transformed with Agrobacterium. Some monocots are more difficult to transform. As previously noted, there are a number of useful transformation processes. The improvements in transformation technology are beginning to eliminate the need to regenerate plants from cells. Since 1986, the transformation of pollen has been published and recently the transformation of plant meristems have been published. The transformation of ovum, pollen, and seedlings meristem greatly reduce the difficulties associated with cell regeneration of different plants or genotypes within a plant can present. Duncan, from at least 1985–1988 produced literature on plant regeneration from callus. Both inbred and hybrid callus have resulted in regenerated plants. Somatic embryogenesis has been performed on various maize tissue which was considered unusable for this purpose. The prior art clearly teaches the regeneration of plants from various maize tissues.

The most common method of transformation is referred to as gunning or microprojectile bombardment. This biolistic process has small gold coated particles coated with DNA shot into the transformable material. Techniques for gunning DNA into cells, tissue, callus, embryos, and the like are well known in the prior art.

After the transformation of the plant material is complete, the next step is identifying the cells or material which has been transformed. In some cases, a screenable marker is employed such as the beta-glucuronidase gene of the uidA locus of *E coli*. Then, the transformed cells expressing the colored protein are selected for either regeneration or further use. In many cases, the transformed material is identified by a selectable marker. The putatively transformed material is exposed to a toxic agent at varying concentrations. The cells which are not transformed with the selectable marker that provides resistance to this toxic agent die. Cells or tissues containing the resistant selectable marker generally proliferate. It has been noted that although selectable markers protect the cells from some of the toxic affects of the herbicide or antibiotic, the cells may still be slightly effected by the toxic agent by having slower growth rates. If the transformed material was cell lines then these lines are regenerated into plants. The cell's lines are treated to induce tissue differentiation. Methods of regeneration of cellular maize material are well known in the art since early 1982. European Patent Application, publication 160,390, describes tissue culture of corn which can be used by those skilled in the art. The plants from either the transformation process or the regeneration process or crossed to either such plants or a progeny of such plants are transgenic plants.

Various techniques known to those skilled in the art, such as haploid, transformation, and a host of other conventional and unconventional methods are within the scope of the invention. All plants and plant cells produced using inbred corn line ZS02234 are within the scope of this invention. The invention encompasses the inbred corn line used in crosses with other, different, corn inbreds to produce (F1) corn hybrid seeds and plants with the characteristics that make good hybrids. This invention includes cells which upon growth and differentiation produce corn plants having the physiological and morphological characteristics of the inbred line ZS02234.

"

A deposit of at least 2500 seeds of the inbred seed of this invention is maintained by Garst, 2369 330th Street, Slater, Iowa 50244. Access to this deposit will be available during the pendency of this application to the Commissioner of Patents and Trademarks and persons determined by the Commissioner to be entitled thereto upon request. The Applicant made a deposit on Jul. 7, 1999, of at least 2500 seeds of Inbred Line ZS02234 with the American Type Culture Collection (ATCC) located at 10801 University Blvd., Massassas, Va. 20110-2209. The ATCC accession number is PTA-318. Additionally, Applicant has satisfied all of the requirements of C.F.R. 1.801–1.809, including providing an indication of the viability of the sample. The ATCC deposit will be maintained in that depository, which is a public depository, for a period of 30 years, or 5 years after the last request, or for the effective life of the patent, whichever is longer, and will be replaced if it becomes nonviable during that period.

Information on some ZS designations may be available from the PVP office.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. Inbred corn seed designated ZS02234, some of said seed deposited in the ATCC and designated accession number PTA-318.

2. A corn plant produced by the seed of claim 1.

3. A tissue culture of regenerable cells of ZS02234 of claim 1 wherein the cells of the tissue culture regenerates plants including phenotype of ZS02234.

4. A tissue culture according to claim 3, the tissue culture selected from the group consisting of leaves, pollen, embryos, roots, root tips, anthers, silk, flowers, kernels, ears, cobs, husks and stalks, and cells and protoplasts thereof.

5. A corn plant capable of expressing the genotype of ZS02234 regenerated from cells of the tissue culture of claim 3.

6. Hybrid seed produced by:
   (a) planting, in pollinating proximity, seeds of corn inbred lines ZS02234 according to claim 1 and another inbred line, one of said inbred lines not releasing pollen;
   (b) cultivating corn plants resulting from said planting;
   (c) allowing natural cross pollinating to occur between said inbred lines; and
   (d) harvesting seeds produced on the non pollen releasing inbred.

7. Hybrid seed produced by hybrid combination of plants of inbred corn seed designated ZS02234 according to claim 1 and plants of another inbred line.

8. Hybrid plants grown from seed of claim 7.

9. A first generation (F1) hybrid corn plant produced by using ZS02234 according to claim 1 the process of:
   (a) planting seeds of corn inbred lines ZS02234 and another inbred line;
   (b) cultivating corn plants resulting from said planting;
   (c) preventing pollen production by the plants of one of the inbred lines;
   (d) allowing pollinating to occur between said inbred lines;
   (e) harvesting seeds produced on plants of the inbred line of step (c); and
   (f) growing a harvested seed of step (e).

10. A tissue culture of the regenerable cells of the corn plant of claim 8.

11. A tissue culture of the regenerable cells of the corn plant of claim 9.

12. An inbred corn plant with all of the phenotypic, physiological and morphological characteristics of inbred corn line of claim 2.

13. An isogenic plant isogenic to the corn plant according to claim 2, said isogenic plant including in said plant at least one transgenic gene selected from the group consisting of *Bacillus Thuringiensis* (Cry) genes expressing insect resistance, and Pat gene, Bar gene, and ESPS gene, expressing herbicide resistance.

14. A seed from the isogenic plant according to claim 13 including at least one of said transgenic genes.

15. An isogenic plant isogenic to the corn plant according to claim 2, including in said isogenic plant at least one mutant gene.

16. A seed from the Isogenic plant according to claim 15.

* * * * *